United States Patent
Frizzell

(10) Patent No.: US 9,795,137 B2
(45) Date of Patent: Oct. 24, 2017

(54) METALAXYL AND PROTHIOCONAZOLE COCRYSTALS AND METHODS OF MAKING AND USING

(71) Applicant: Bayer CropScience LP, Research Triangle Park, NC (US)

(72) Inventor: David Frizzell, Holt, MO (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 14/391,749

(22) PCT Filed: Mar. 12, 2013

(86) PCT No.: PCT/US2013/030346
§ 371 (c)(1),
(2) Date: Oct. 10, 2014

(87) PCT Pub. No.: WO2013/162725
PCT Pub. Date: Oct. 31, 2013

(65) Prior Publication Data
US 2015/0064257 A1  Mar. 5, 2015

Related U.S. Application Data

(60) Provisional application No. 61/638,196, filed on Apr. 25, 2012, provisional application No. 61/726,619, filed on Nov. 15, 2012.

(51) Int. Cl.
A61K 9/14 (2006.01)
A01N 43/653 (2006.01)
A01N 25/12 (2006.01)
A01N 37/26 (2006.01)

(52) U.S. Cl.
CPC ........... *A01N 43/653* (2013.01); *A01N 25/12* (2013.01); *A01N 37/26* (2013.01)

(58) Field of Classification Search
USPC ........................................................ 424/489
See application file for complete search history.

(56) References Cited

U.S. PATENT DOCUMENTS 7,683,086 B2 * 3/2010 Ammermann et al. ...... 514/384
2010/0113543 A1 * 5/2010 Israels .................... A01N 47/34
514/383

OTHER PUBLICATIONS

Miroshnyk (Expert Opin. Drug Deliv. (2009) 6(4), pp. 333-341).*

* cited by examiner

*Primary Examiner* — Devang Thakor

(57) ABSTRACT

The invention relates to co-crystals of metalaxyl and prothioconazole, to methods of making them, to compositions containing them and to the methods of using said co-crystals and said compositions to treat crops and plants.

20 Claims, 11 Drawing Sheets

METALAXYL AND PROTHIOCONAZOLE COCRYSTALS AND METHODS OF MAKING AND USING

CROSS REFERENCE TO RELATED APPLICATIONS

This application claims priority to U.S. Provisional Application No. 61/638,196, filed on Apr. 25, 2012, and U.S. Provisional Application No. 61/726,619, filed on Nov. 15, 2012, the contents of each which are incorporated herein by reference in their entirety.

FIELD

Cocrystal metalaxyl and prothioconazole compounds and compositions thereof are described herein. Methods for forming crystalline compounds are also described. The disclosure also provides for methods of using compounds and compositions described herein to treat crops, plants, and seeds.

BACKGROUND

Some pesticides, fungicides, and insecticides are known to have a high water solubility and are therefore susceptible to mobility and/or runoff from treated areas. The runoff associated with the application of many pesticides, fungicides, and insecticides has the potential to seep into groundwater and negatively impact the environment. Because of the mobility, higher concentrations of pesticides, fungicides, and insecticides are oftentimes applied to seeds and plants to ensure that a sufficient amount of active ingredient is available for utilization by the plant. Accordingly, there is a need to develop compounds and compositions that exhibit lower water solubility.

SUMMARY

In an aspect, the disclosure provides for a prothioconazole and metalaxyl cocrystal compound. In another aspect, the cocrystal has a melting point of about 100.8° when measured with a Differential Scanning calorimeter. In another aspect, the cocrystal is about 0.1 µm to about 100 µm. In yet another aspect, the cocrystal exhibits the Differential Scanning calorimeter profile of FIG. 5 when crystallized from a butyrolactone solution or FIG. 6 from an acetone solution.

The disclosure also provides for a method of making a cocrystal comprising
(a) dissolving metalaxyl and prothioconazole in a solvent; and
(b) crystallizing the dissolved metalaxyl and prothioconazole.

In another aspect, the dissolved metalaxyl and prothioconazole is crystallized by the addition of a low solubility solvent, water, by altering the temperature, by freezing, or by seeding.

The disclosure also provides for a method of reducing damage or infestation caused by weeds, fungi, or pests by applying a cocrystal including prothioconazole and metalaxyl or a composition comprising said cocrystals to a crop, plant, or seed. In an aspect, the cocrystal is applied to a crop, plant, or seed in an amount sufficient to treat a pest or weed infestation to crop, plant, or seed. In another aspect, the cocrystal is applied to a crop, plant, or seed from about 0.5 fluid ounces/acre to about 10.0 fluid ounces/acre. In another aspect, the crop is selected from the group consisting cereals, barley, wheat, winter wheat, triticale winter rye, ground nut, peanuts, rape, bulb onions, oilseed rape, canola, rice, pulses, soybeans, sugar beet, vegetables, and corn.

DETAILED DESCRIPTION

The disclosure provides for a cocrystal comprising, consisting of, or consisting essentially of prothioconazole and metalaxyl. In another aspect, the disclosure provides for a composition comprising, consisting of, or consisting essentially of a cocrystal of prothioconazole and metalaxyl.

Figure 5:
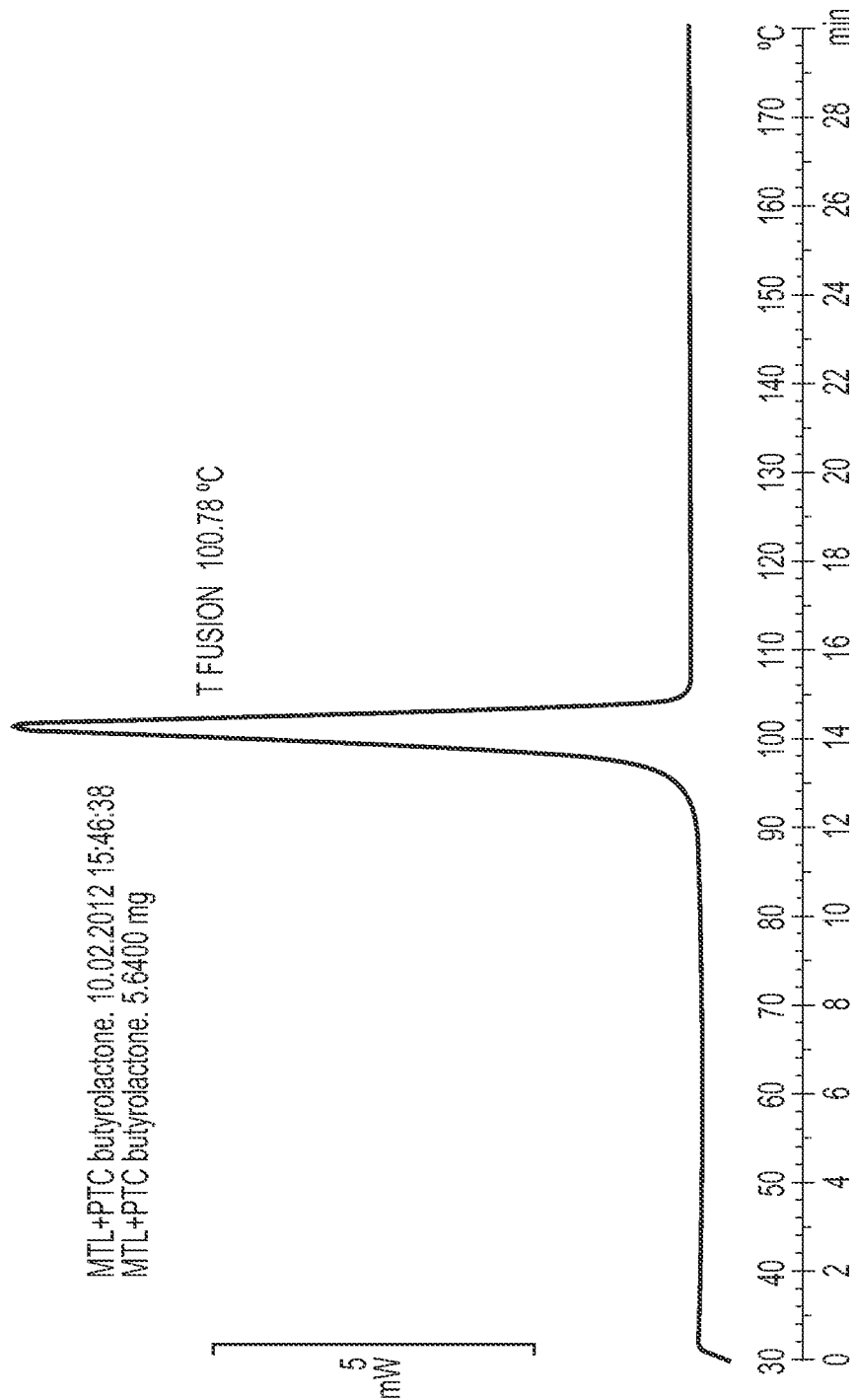
FIG. 5 describes a 30° C. to 180° C. at 5° C./minute differential scanning calorimeter (DSC) scan of a prothioconazole and metalaxyl cocrystal sample created from a butyrolactone solution.
Figure 6:
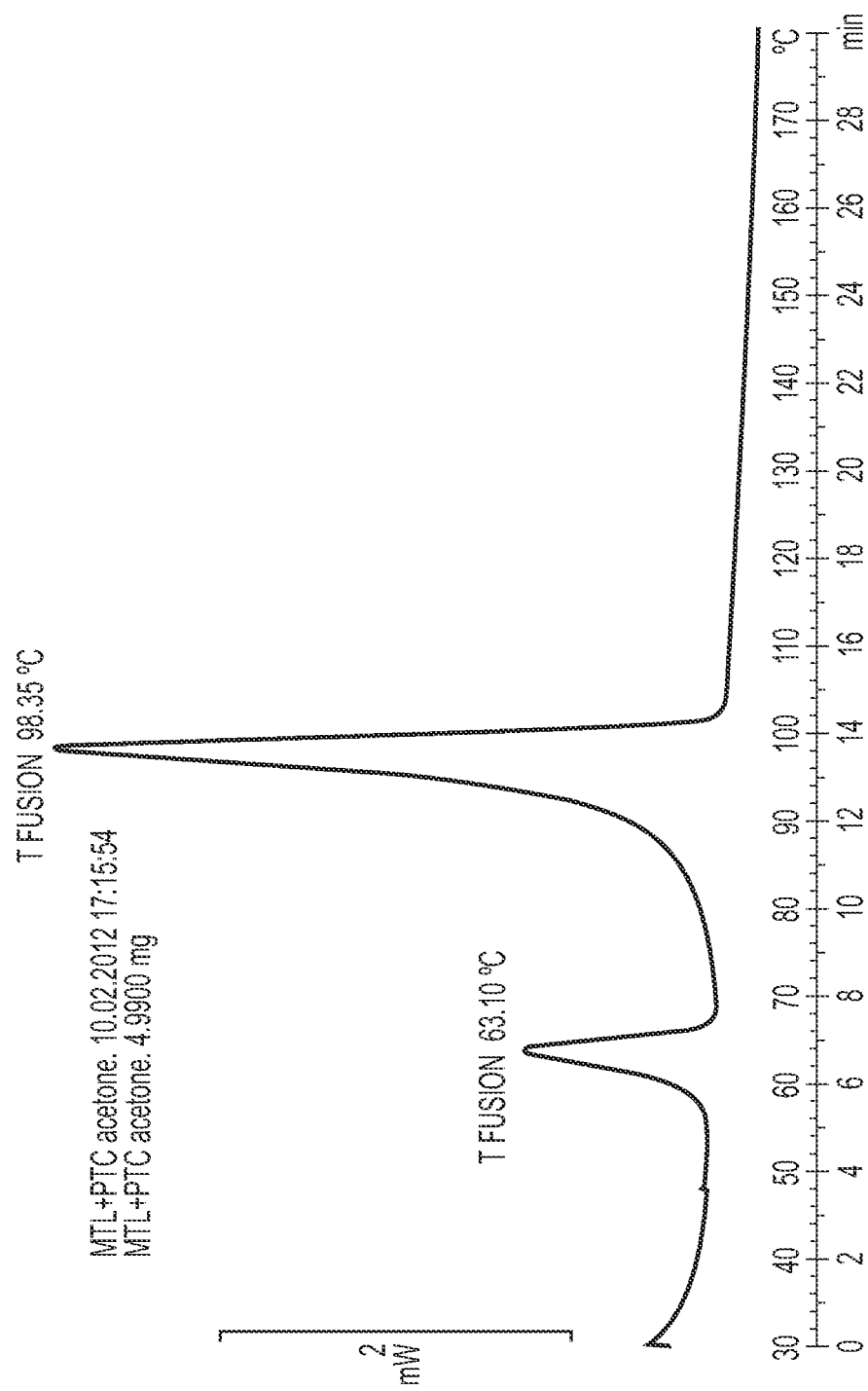
FIG. 6 describes a 30° C. to 180° C. at 5° C./minute DSC scan of a prothioconazole and metalaxyl cocrystal sample created from an acetone solution.
Figure 8:
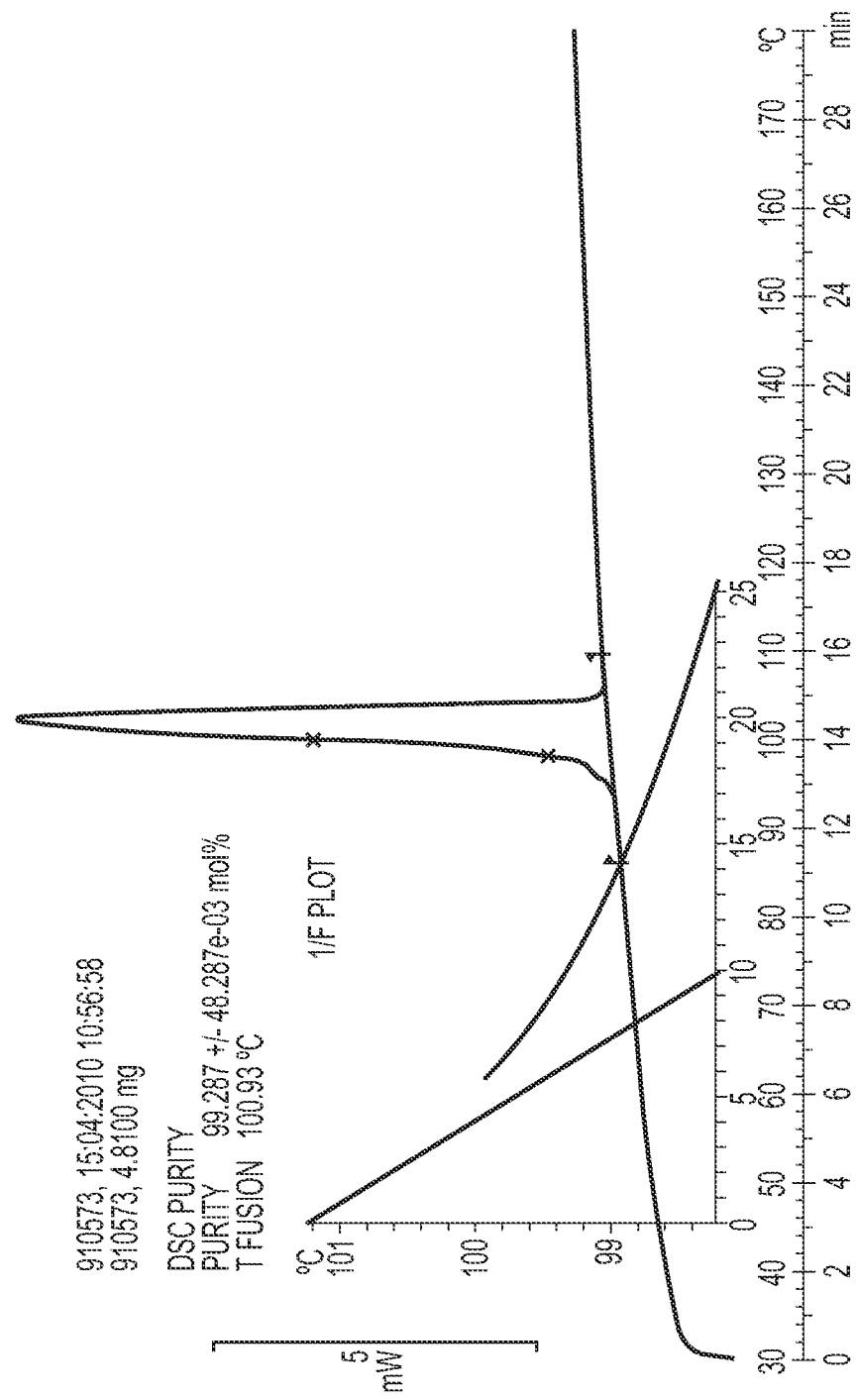
FIG. 8 describes a 30° C. to 180° C. at 5° C./minute DSC scan of a prothioconazole and metalaxyl cocrystal sample.

The disclosure also provides for a cocrystal comprising, consisting of, or consisting essentially of prothioconazole and metalaxyl, wherein the cocrystal has a melting point of about 100.8° C. when measured with a Differential Scanning calorimeter. The melting point of a material is dependent on the purity of the material. For example, the more pure the substance, the higher the expected melting point. FIG. 5 and FIG. 8 exhibit a relatively high purity of material based on the upward slope of the heatflows in the respective scans. The higher purity material also has a melting point (heat of fusion) temperature of about 100.8° C.-100.9° C. FIG. 6 has a lower purity cocrystal material with a 98.4° C. melting point and exhibit a more shallow slop on the heat flow scan.

In an aspect, the disclosure also provides for a cocrystal comprising, consisting of, or consisting essentially of prothioconazole and metalaxyl, wherein the cocrystal has a melting point of about 95° C. to about 105° C., about 98° C. to about 102° C., or about 100° C. to about 101° C. when measured with a Differential Scanning calorimeter.

Figure 1B:
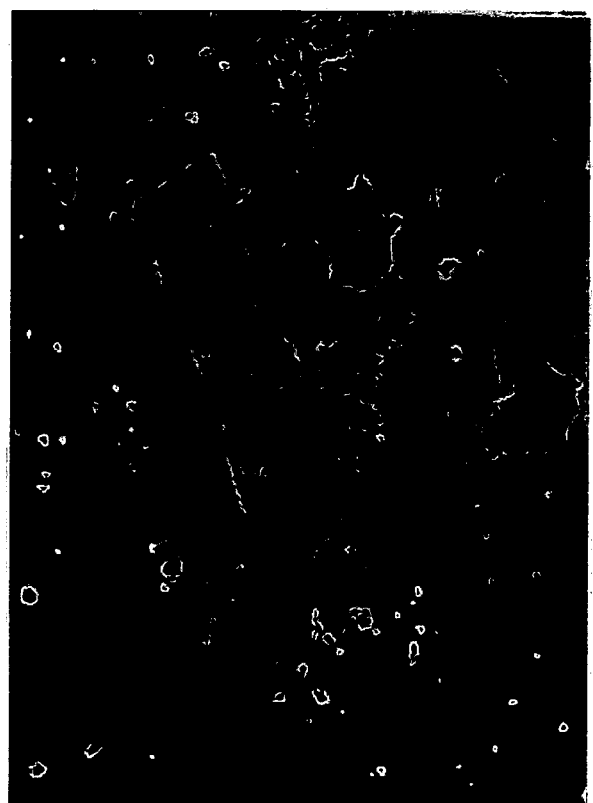
FIGS. 1 A and B sets forth micrographs of prothioconazole and metalaxyl cocrystals formed by methods of the description.
Figure 1A:
Figure 2:
FIG. 2 sets forth a micrograph of prothioconazole and metalaxyl cocrystals with a 1 mm glass sphere used as a reference.
Figure 3:
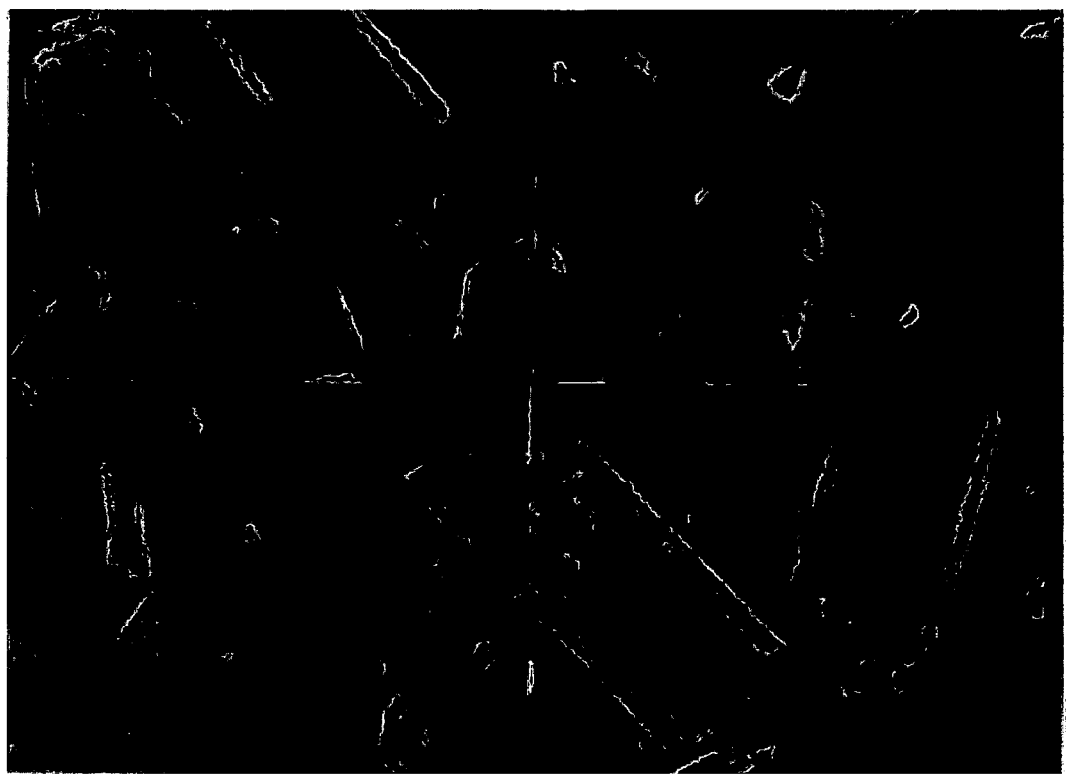
FIG. 3 sets forth a micrograph of prothioconazole and metalaxyl cocrystals formed by methods of the description. The Differential Scanning calorimeter scan of these cocrystals is set forth in FIG. 8.
Figure 4:
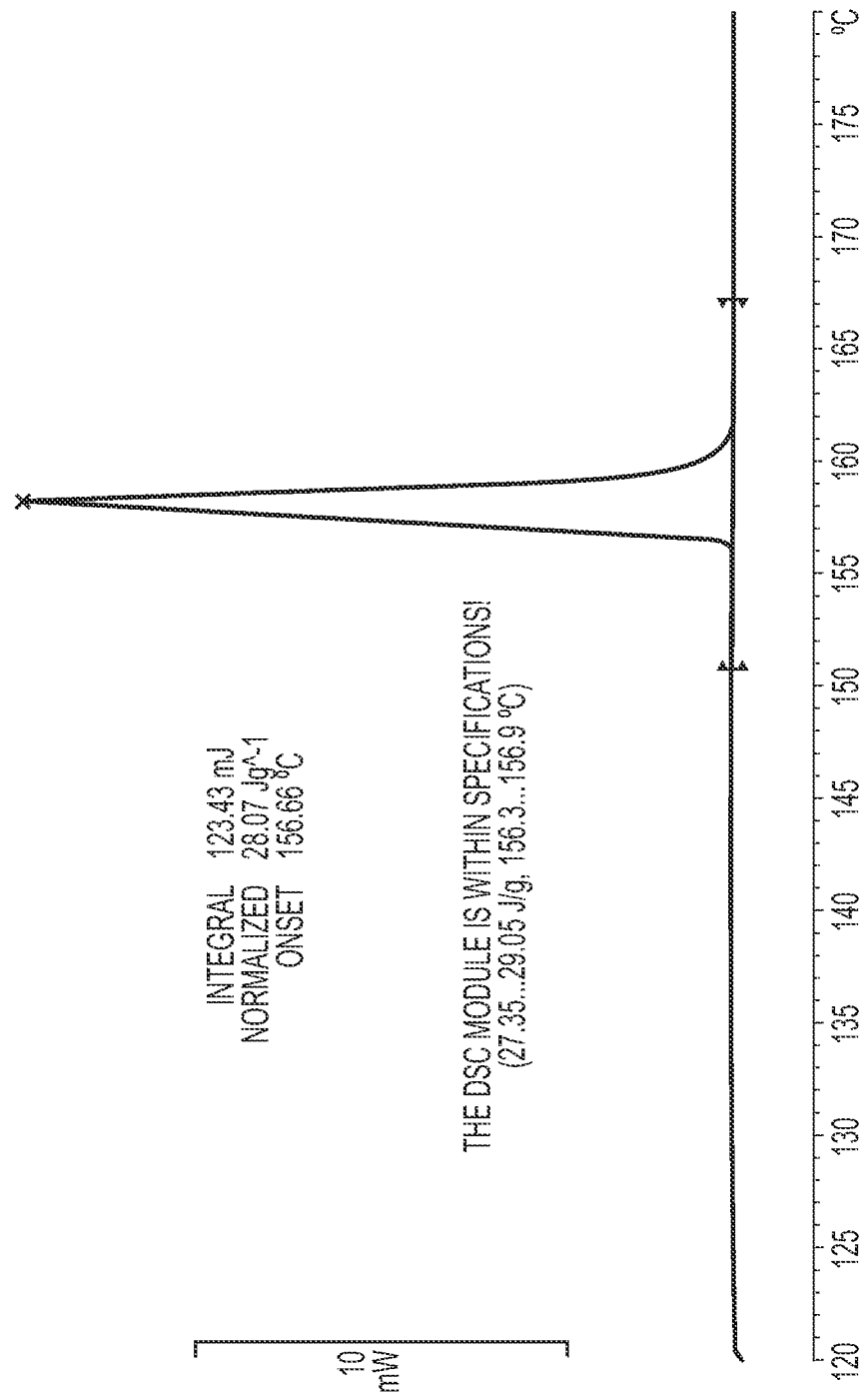
FIG. 4 sets forth the calibration of the Differential Scanning calorimeter instrument using the Mettler program "check DSC ^ end In" using 6.32 mg In metal standard.

In another aspect, the disclosure provides for a cocrystal comprising, consisting of, or consisting essentially of prothioconazole and metalaxyl with the crystal structure as set forth in FIG. 1, 2, or 3. In yet another aspect, the disclosure provides for a cocrystal comprising, consisting of, or consisting essentially of prothioconazole and metalaxyl with the Differential Scanning calorimeter parameters of FIG. 5, 6, or 8.

The disclosure also provides for a cocrystal composition comprising, consisting of, or consisting essentially of prothioconazole and metalaxyl wherein the water solubility of the crystal composition is less than that of metalaxyl (about 8.4 g/l at 22° C.), prothioconazole (610 μg/l at 25° C.), or a combination of metalaxyl and prothioconazole. In an aspect, the water solubility measurements are at pH 7.0. In another aspect, the prothioconazole and metalaxyl crystal composition has a reduced water solubility that is reduced by about 5%, about 10%, about 20%, about 30%, about 50%, about 60%, about 70%, about 80%, about 90%, about 95%, or about 99% or more relative to the water solubility of metalaxyl alone. In yet another aspect, the prothioconazole and metalaxyl crystal composition has a reduced water solubility that is reduced by about five times, about ten times, about fifteen times, about twenty times, about twenty-five times, about thirty times, or about forty times or more relative to the water solubility of metalaxyl alone. Such relatively low water solubility reduces runoff and active agent mobility from treated areas. Such relatively low water solubility reduces runoff and active agent mobility from treated areas.

Figure 9A:
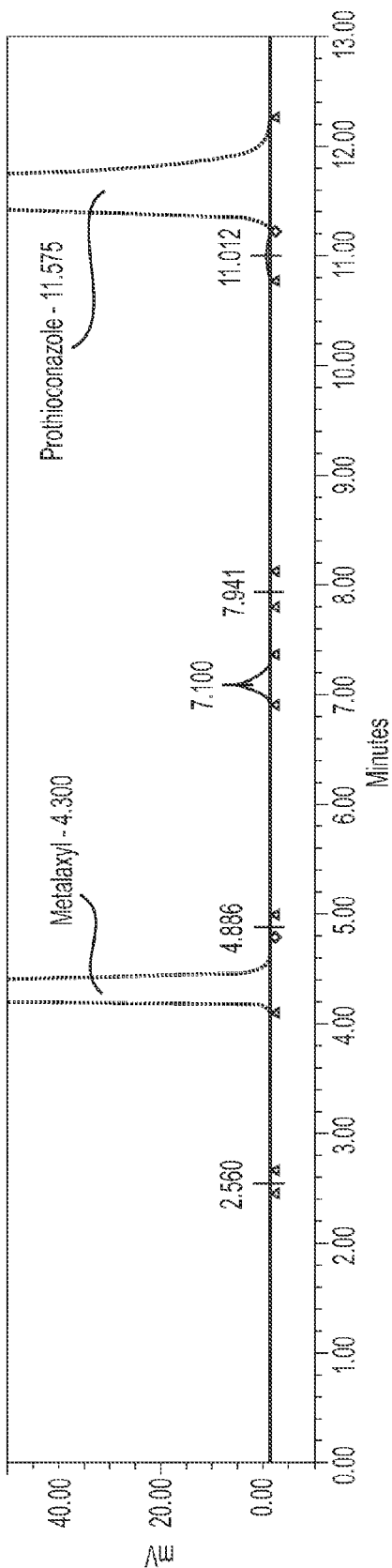
FIG. 9 describes a HPLC scan of a prothioconazole and metalaxyl standard sample.
Figure 9B:
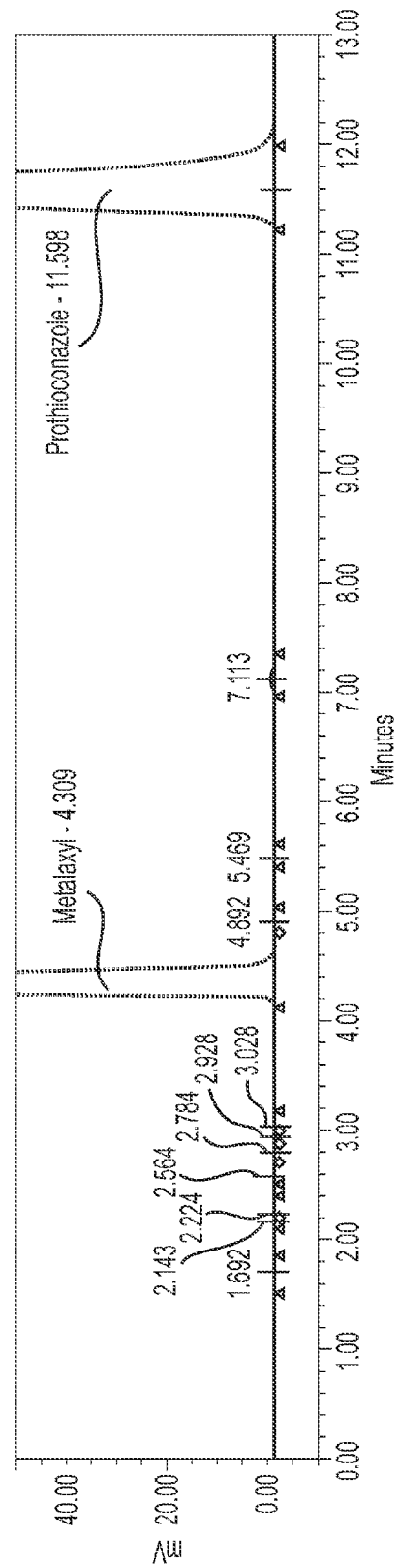

In another aspect, the prothioconazole and metalaxyl crystal composition has an increased water solubility that is increased by about 5%, about 10%, about 20%, about 30%, about 50%, about 60%, about 70%, about 80%, about 90%, about 95%, or about 99% or more relative to the water solubility of prothioconazole alone. In yet another aspect, the prothioconazole and metalaxyl crystal composition has an increased water solubility that is increased by about five times, about ten times, about twelve times, about thirteen times, about fifteen times, or about twenty times or more relative to the water solubility of prothioconazole alone. Examples 5 and 6 and FIG. 9(A), FIGS. 10(A) and (B), and FIGS. 11 (A), (B), and (C) provide support for the increased prothioconazole solubility and decreased metalaxyl solubility of the crystal compositions described herein. Such an increased solubility of prothioconazole is unexpected and can result in a composition where the metalaxyl exhibits a decreased solubility and the prothioconazole exhibits an increased solubility. In an aspect, the prothioconazole and metalaxyl crystal composition will have increased bioavailability of prothioconazole together with a decreased bioavailability of metalaxyl. In another aspect, the prothioconazole and metalaxyl crystal composition exhibits decreased metalaxyl solubility wherein the metalaxyl has the ability to stay with the plant longer while reducing metalaxyl seepage into groundwater.

Metalaxyl, N-(2,6-dimethylphenyl)-N-(methoxyacetyl)-DL-alanine methyl ester, is represented by the formula of:

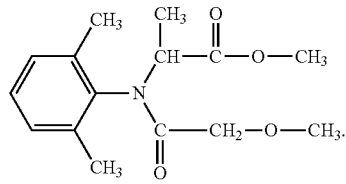 [SMILES: COCC(=O)N(c1c(C)cccc1C)C(C)C(=O)OC]

Prothioconazole, 2-[2-(1-chlorocyclopropyl)-3-(2-chlorophenyl)-2-hydroxypropyl]-1,2-dihydro-3H-1,2,4-triazole-3-thione, is represented by the formula of:

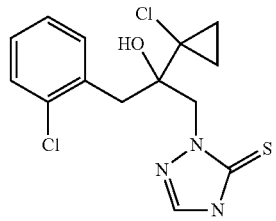 [SMILES: OC(Cc1ccccc1Cl)(Cn1nc[nH]c1=S)C1(Cl)CC1]

In an aspect, the cocrystal structures described herein comprise metalaxyl and prothioconazole in about a 44:52 ratio or about a 1:1 molar basis. In another aspect, the cocrystal structures described herein comprise metalaxyl and prothioconazole in about a 1:1 molar basis.

In an aspect, the disclosure provides for a method of making a metalaxyl and prothioconazole cocrystal by dissolving metalaxyl and prothioconazole in a solvent. In another aspect, the disclosure provides for a method of making a metalaxyl and prothioconazole cocrystal composition by
  (a) dissolving metalaxyl and prothioconazole in one or more solvents; and
  (b) crystallizing the dissolved metalaxyl and prothioconazole.

The disclosure also provides for a method of making a metalaxyl and prothioconazole cocrystal by
  (a) dissolving metalaxyl and prothioconazole in one or more solvents; and
  (b) adding a solvent that is less soluble than the dissolved metalaxyl and prothioconazole solution to the dissolved metalaxyl and prothioconazole in an amount sufficient to induce crystallization.

The disclosure also provides for a method of making a metalaxyl and prothioconazole cocrystal by
  (a) dissolving metalaxyl and prothioconazole in one or more solvents; and
  (b) adding water to the dissolved metalaxyl and prothioconazole in an amount sufficient to induce crystallization.

In an another aspect, the disclosure provides for a method of making a metalaxyl and prothioconazole cocrystal by
  (a) dissolving metalaxyl and prothioconazole in one or more solvents;
  (b) adding water to the dissolved metalaxyl and prothioconazole in an amount sufficient to form crystals; and
  (c) adding an additional amount of water to the crystallized material.

In another aspect, the disclosure provides for a method of making a metalaxyl and prothioconazole cocrystal by
  (a) dissolving metalaxyl and prothioconazole in one or more solvents; and (b) altering the temperature of the dissolved metalaxyl and prothioconazole composition in a manner that produces a metalaxyl and prothioconazole cocrystal composition.

In an aspect, the compounds described herein can be crystallized by any known crystallization method, for example, crystallization by altering temperature, increasing temperature, decreasing temperature, a combination of increasing and decreasing temperature, freezing, or by initiating solvent-induced crystallization. The disclosure also provides for a method of crystallizing compounds described herein by seeding by any known technique. In another aspect, the compounds described herein can be crystallized by adding a preformed cocrystal to a saturated solution thereby seeding the solution. In another aspect, about 1% or less, about 2% or less, about 5% or less, or about 10% or less of the preformed cocrystal is used to seed the solution and facilitate cocrystal formation.

In an aspect, the crystallization solvent used with the methods described herein include one or more organic or polar solvents. In another aspect, the solvent used with the methods described herein is selected from the group consisting of butyrolactone and acetone. Other solvents that may be used with the methods described herein, for example, include aliphatic hydrocarbons, aromatic hydrocarbons, halogenated hydrocarbons such as toluene, xylene, mineral oils such as white spirit, petroleum, alkylbenzenes and spindle oil, tetrachloromethane, chloroform, methylene chloride and dichloromethane, esters such as ethyl acetate, lactates, lactones, lactams such as N-methylpyrrolidone, N-octylpyrrolidone, N-dodecylpyrrolidone, N-octylcaprolactam and N-methylcaprolactam, gamma-butyrolactone, dimethylformamide, tributyl phosphate, acetonitrile, dichloromethane, dimethylsulfoxide, ethyl acetate, n-heptane, 1-octanol, polyethylene glycol, or 2-propanol. In an aspect, the solvent is added in an amount that is sufficient to crystallize the active agent, for example, metalaxyl and prothioconazole.

In another aspect, the cocrystals described herein exhibit a diameter of about 0.01 µm to about 100 µm, about 0.1 µm to about 50 µm, about 1 µm to about 20 µm, or about 2 µm to about 10 µm.

Further compounds or actives capable of being crystallized in the compositions or methods described herein include triazolyl derivatives such as those described in U.S. Pat. No. 5,789,430, and compounds described in U.S. Pat. No. 4,742,079, the contents of each of these applications is herein incorporated by reference in their entirety.

In an aspect, the disclosure provides for a method of treating a crop, plant, seed, or plant part with a cocrystal or composition described herein. In yet another aspect, the disclosure provides for a method of reducing phytotoxicity to a crop, plant, seed, or plant part by the application of a cocrystal or composition described herein. In another aspect, the disclosure provides for a method of reducing damage or infestation caused by weeds, fungi, or pests by applying a cocrystal or composition described herein to a to a crop, plant, seed, or plant part thereof. In yet another aspect, the disclosure provides for a method of improving crop yield by the application of a cocrystal or composition described herein. In yet another aspect, a cocrystal or composition described herein is a time released or delayed release composition. In an aspect, pests include, for example, insects, mites, phytopathogenic fungi, or bacteria.

In another aspect, a cocrystal or composition described herein is applied to a crop, plant, seed, or plant part thereof in a single application step. In another aspect, a cocrystal or composition described herein is applied in multiple application steps to a crop, plant, seed, or plant part thereof. In yet another aspect, a cocrystal or composition described herein is applied in one, two, three or more application steps to a crop, plant, seed, or plant part thereof.

The cocrystals or compositions described herein can be used in an amount effective to increase plant or crop yield, reduce phytotoxicity to a crop, plant, seed, or plant part, or reduce damage or infestation caused by weeds, fungi, or pests. In an aspect, a cocrystal or composition described herein is applied at about 0.5 fluid ounces/acre to about 10.0 fluid ounces/acre, about 1.0 fluid ounces/acre to about 8.0 fluid ounces/acre, about 2.0 fluid ounces/acre to about 6.0 fluid ounces/acre, or about 3.0 fluid ounces/acre to about 5.0 fluid ounces/acre. In another aspect, a cocrystal or composition described herein is applied at about 0.1, about 1.0, about 2.0, about 3.0, about 4.0, about 5.0, about 6.0, about 7.0, about 8.0, about 9.0, about 10.0, or about 20.0 or more fluid ounces/acre. In yet another aspect, a cocrystal or composition described herein is applied at about 0.1, about 1.0, about 2.0, about 3.0, about 4.0, about 5.0, about 6.0, about 7.0, about 8.0, about 9.0, about 10.0, or about 20.0 fluid ounces/acre.

In another aspect, a cocrystal or composition described herein is applied to a crop, plant, seed, or plant part at planting. In another aspect, a cocrystal or composition described herein is applied to a crop, plant, seed, or plant part at about 5 to about 10, about 5 to about 15, about 7 to about 14, about 5 to about 20, about 10 to about 30 days, about 10 to about 40 days, about 15 to about 25 days, or about 20 to about 40 days after planting. In another aspect, a cocrystal or composition described herein is applied to a crop, plant, seed, or plant part described herein at about 5, about 10, about 15, about 20, about 25, about 30, or about 50 or more days after planting. In yet another aspect, a composition described herein is applied to a crop, plant, seed, or plant part described herein at least 5, at least 10, at least 15, at least 20, at least 25, at least 30, or at least 50 after planting.

In an aspect, the methods disclosed herein reduce damage caused by a weed, fungi, or pest by about 10% to about 20%, about 10% to about 30%, about 10% to about 40%, about 10% to about 90%, about 20% to about 80%, about 30% to about 70%, about 40% to about 60%, or about 5% or more, about 10% or more, about 20% or more, about 30% or more, about 40% or more, about 50% or more, about 60% or more, about 70% or more, about 80% or more, or about 90% or more, about 5% or less, about 10% or less, about 20% or less, about 30% or less, about 40% or less, about 50% or less, about 60% or less, about 70% or less, about 80% or less, or about 90%. In yet another aspect, the methods, compounds, and compositions disclosed herein reduce damage caused by a weed, fungi, or pest described herein by about 5%, about 10%, about 20%, about 30%, about 40%, about 50%, about 60% about 70%, about 80%, or about 90%. In another aspect, the above percentages are relative to an untreated plant.

In an aspect, binders, coating agents, wetting agents, or buffering agents can be added to a composition described herein. In another aspect, at least one agriculturally acceptable carrier can be added to the formulation such as water, solids, or dry powders. The dry powders can be derived from a variety of materials such as wood barks, calcium carbonate, gypsum, vermiculite, talc, humus, activated charcoal, and various phosphorous compounds. In an aspect, a composition described herein can include a spray or tank mix adjuvant. In another aspect, a composition described herein can include additional components, such as an insecticide, fungicide, herbicides, fertilizer, or foliar-applied fertilizers. In another aspect, compositions described herein can include methylated seed oil ("MSO"), for example MSO at 0.5% v/v to 1.0% v/v. In yet another aspect, compositions described herein can contain High Surfactant Oil Concentrates ("HSOC") or Crop Oil Concentration ("COC"). In another aspect, MSO is a tank mix adjuvant capable of being used with a composition described herein.

Compositions described herein may also be combined with additional fungicides, pesticides, herbicides, or insecticides. In an another aspect, compositions described herein may be combined with, for example, chlorothalonil; clothianidin; copper hydroxide; copper oxide; copper oxychloride; furathiocarb; imazalil; imidacloprid; ipconazole; mancozeb; metconazole; myclobutanil; PCNB; prothioconazole; pyraclostrobin; TCMTB; tebuconazole; thiabendazole; thiram; triadimefon; triadimenol; trifloxystrobin; or triticonazole.

In an aspect, the compositions described herein can include about 0.1% to about 2%, about 5% to about 10%, about 10% to about 30%, about 20% to about 50%, or about 50% to about 90% percent, or about 0.1% to about 90% percent by weight of a binder, coating agent, wetting agent, solvent, carrier, or buffering agent described herein. In an another aspect, the compositions described herein can include about 0.1% to about 2%, about 10% to about 30%, about 20% to about 50%, or about 0.1% to about 90% percent by weight of an additional fungicide, pesticide, herbicide, or insecticide described herein. In yet another aspect, the compositions described herein can include about 0.01% to about 0.5%, about 1% to about 2%, about 2% to about 4%, about 5% to about 10%, about 20% to about 50% percent by weight of a cocrystal described herein.

In yet another aspect, the compositions described herein can include about 0.01% to about 0.5%, about 1% to about 2%, about 2% to about 4%, about 5% to about 10%, about 20% to about 50% percent, or about 0.1% to about 90% percent by weight by weight of a cocrystal described herein. In another aspect, the compositions described herein can include about 1%, about 2%, about 5%, about 10%, about 20%, about 50%, about 75%, or about 0.1% to about 90% percent by weight of more by weight of a cocrystal described herein.

In an aspect, components of compositions described herein can be converted into customary formulations, such as, emulsions, wettable powders, suspensions, suspension concentrate, powders, dusts, pastes, soluble powders, granules, suspoemulsion concentrates, natural and synthetic materials impregnated with active compound, and ultrafine encapsulations in polymeric materials. In the case of the use of water as an extender, organic solvents can, for example, also be used as cosolvents in compositions described herein. Liquid solvents which are suitable include: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral oils and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and water.

Solid carriers which are suitable are for example, ammonium salts and ground natural minerals, such as kaolins, clays, talc, chalk, quartz, attapulgite, montmorillonite or diatomaceous earth, and ground synthetic minerals, such as highly-disperse silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersants are: for example lignin-sulphite waste liquors and methylcellulose.

In one embodiment, plant species and plant varieties which are found in the wild or which are obtained by traditional biological breeding methods, such as hybridization or protoplast fusion, and parts of these species and varieties are treated. In a further preferred embodiment, transgenic plants and plant varieties which were obtained by recombinant methods, if appropriate in combination with traditional methods (genetically modified organisms) and their parts can be treated.

Crops, plants, seeds, or plant parts thereof which can be treated by the compositions or methods described herein include, for example, any plant capable of being effectively treated by a cocrystal comprising prothioconazole or metalaxyl individually or together. Examples of crops, plants, seeds, or plant parts which can be treated by the compositions or methods described herein include, for example, cereals, barley, wheat, winter wheat, triticale winter rye, ground nut, peanuts, rape, bulb onions, oilseed rape, canola, rice, pulses, soybeans, sugar beet, vegetables, and corn. In an aspect, the seeds or plants described herein can be treated in an amount effective to confer the desired solubility property. In another aspect, the seeds or plants described herein can be treated in an amount described herein.

In another aspect, the disclosure provides for a method of treating a seed, for example a plant seed, with a composition described herein. In yet another aspect, the seed is a soybean or corn seed.

The plants and their parts may be treated with the described compositions by applying the compositions directly to the plants or plant parts. In another embodiment, the plant and plant parts may be treated indirectly, for example by treating the environment or habitat in which the plant parts are exposed to. Conventional treatment methods may be used to treat the environment or habitat including dipping, spraying, fumigating, chemigating, fogging, scattering, brushing on, shanking or injecting.

In another aspect, the disclosure provides for a kit comprising, consisting essentially of, or consisting of any of the cocrystal or compositions disclosed herein. In an aspect, the kit includes any of the combination of the cocrystals or compositions described in Examples 1-7 or FIGS. 1-11. In another aspect, the kit provides for the cocrystals compositions described in Examples 1-7 and FIGS. 1-11 applied in a manner that is consistent with the methodology of these examples and figures. In another aspect, the kit provides instructions or guidance regarding the use of the cocrystals, compositions, or methods described herein.

In an aspect, the kit includes instructions describing the methodology described herein. In another aspect, the kit includes instructions describing the methodology set forth in any of Examples 1-7 and FIGS. 1-11. In an aspect, the instructions are included with the kit, separate from the kit, in the kit, or are included on the kit packaging.

The following examples serve to illustrate certain aspects of the disclosure and are not intended to limit the disclosure.

EXAMPLES

Example 1

Example 1 sets forth the co-crystallization of Prothioconazole and Metalaxyl crystallized from a butyrolactone solution.

0.5 g Prothioconazole (98.4% pure) and 0.5 g Metalaxyl (98.2% pure) were placed into a 0.5 oz. bottle. Butyrolactone (Aldrich BIO, 360-8) was added in an amount sufficient to dissolve the Prothioconazole and Metalaxyl (~3 mL). Water (DI) was added dropwise to the mixture and tan to off-white crystals appeared. About 10 mL of additional water was added to the mixture. The crystals were filtered from the liquid using a porous glass filter and washed water. The crystals were dried in a 60° vacuum oven at about 23" Hg vacuum. The yield was found to be 0.9 g.

The prothioconazole and metalaxyl sample in butyrolactone was weighed into a 40 µL aluminum crucible and closed with a pierced cap. The melting point of the prothioconazole is approximately 140° C. and the melting point of the metalaxyl is approximately 70° C. The sample was heated from 30° C. to 180° C. at 5° C./minute. As set forth in FIG. 5, a Differential scanning calorimetry scan shows a sharp exotherm from the melt at 89-109° C. (temperature of fusion at about 100.8° C.).

Example 2

Example 2 sets forth the co-crystallization of Prothioconazole and Metalaxyl crystallized from an acetone solution.

0.5 g Prothioconazole (98.4% pure) and 0.5 g Metalaxyl (98.2% pure) were placed into a 0.5 oz. bottle. Acetone was added in an amount sufficient to dissolve the Prothioconazole and Metalaxyl (~3 mL). Water (DI) was added dropwise to the mixture and dark tan to off-white crystals appeared. Compared to the crystals of Example 1, the crystals identified in Example 2 were stickier and exhibited an increased variation in color. About 10 mL of additional water was added to the mixture. The crystals were filtered from the liquid using a porous glass filter and washed water. The crystals were dried in a 60° C. vacuum oven at about 23" Hg vacuum. Once dry, the crystals were no longer sticky and were easily dispersed into a powder form.

The prothioconazole and metalaxyl in acetone sample was weighed into a 40 µL aluminum crucible and closed with a pierced cap. The sample was heated from 30° C. to 180° C. at 5° C./minute. A small endotherm was observed at 58° C. to 68° C. and a larger endotherm from 70° C. to 104° C. As set forth in FIG. 6, a peak is present at about 63.10° C. This peak is expected to be in the range of a metalaxyl melt. So we have some metalaxyl not in the cocrystal lattice in this DSC scan. The DSC scan of FIG. 6 also includes cocrystal at 98.4° C.

Example 3

Example 3 sets forth a Differential scanning calorimetry scan of Metalaxyl and Prothioconazole.

Figure 7:
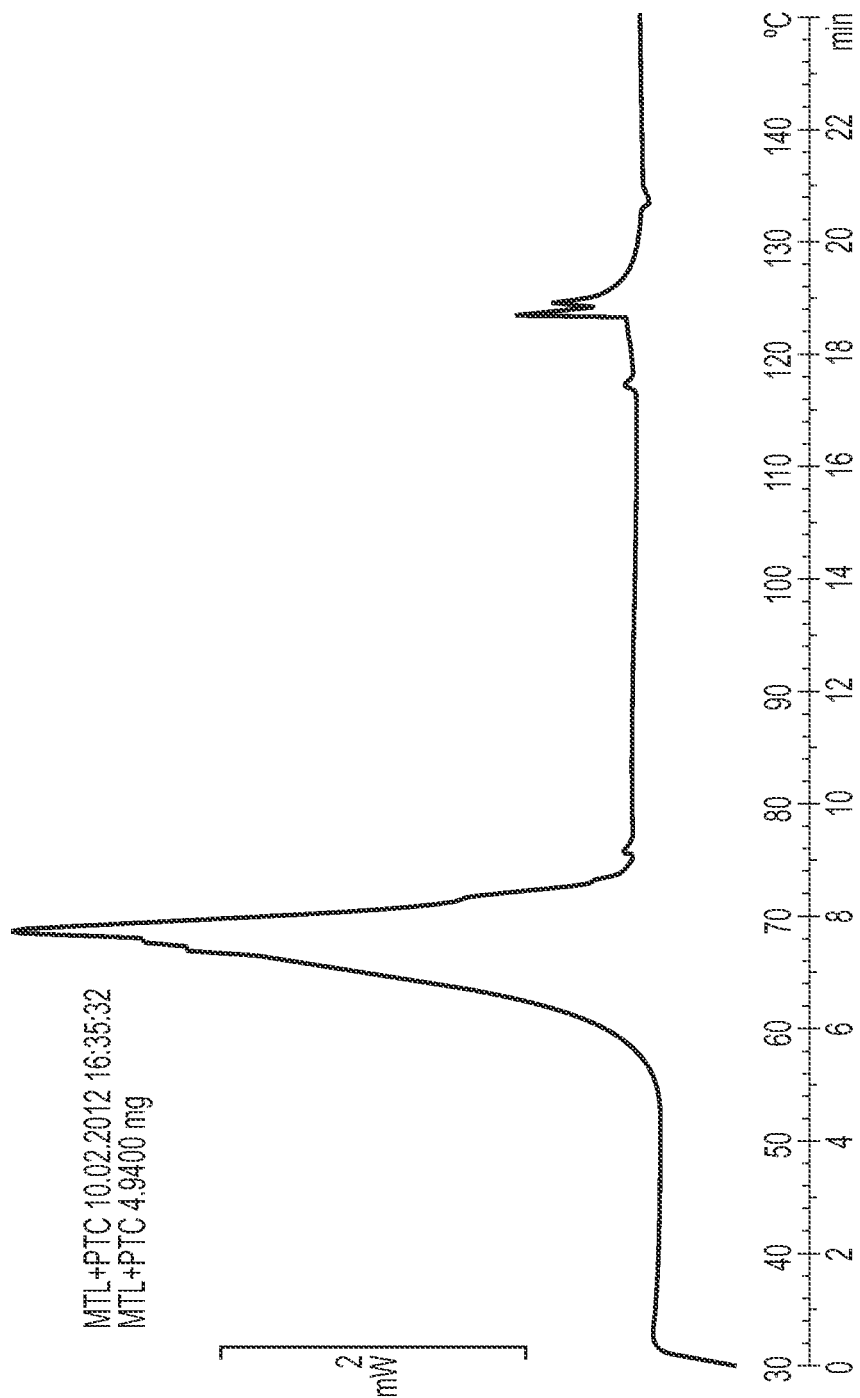
FIG. 7 describes a 30° C. to 150° C. at 5° C./minute DSC scan of a non-cocrystallized prothioconazole and metalaxyl, (weighed separately into the crucible prior to doing the DSC scan).

Metalaxyl and prothioconazole were combined into a single crucible without crystallization. A Differential scanning calorimetry scan was run on the metalaxyl and prothioconazole as a control. The prothioconazole and metalaxyl sample heated from 30° C. to 150° C. at 5° C./minute. An endotherm was observed at 55° C. to 78° C. and a small double endotherm at 124° C. and 132° C. (FIG. 7). FIG. 7 exhibits a peak at the melting point of metalaxyl and another at the melting point of prothioconazole.

Example 4

Example 4 sets forth Microphotographs of Cocrystals of Metalaxyl and Prothioconazole.

The particulate matter retained on the sieves from Example 1 was microphotographed and is illustrated in FIGS. 1 A and B and FIG. 2. An additional microphotograph of the crystals along with a 1-mm glass sphere is found in FIG. 3. The crystals of FIG. 3 corresponds to the DSC of FIG. 8.

Example 5

Example 5 provides for Metalaxyl and Prothioconazole water solubility measurements.

A saturated solution of metalaxyl and prothioconazole as separate compounds was prepared by the following procedure: 0.2 grams each of metalaxyl and prothioconazole were weighed and placed into a 0.5 oz bottle. 10 mL of pH 7.0 (Fisher #SB107-500) was added to the bottle. A magnetic stir bar was added to the bottle and the bottle was capped and shaken. The bottle was placed on a magnetic stirrer for about 12 hours at a temperature of 20° C.±1° C. stirring on low. After the above procedure, the solubility of metalaxyl at pH 7.0 was measured as 0.62% and the solubility of prothioconazole at pH 7.0 was measured as 0.0002%.

Figure 10A:
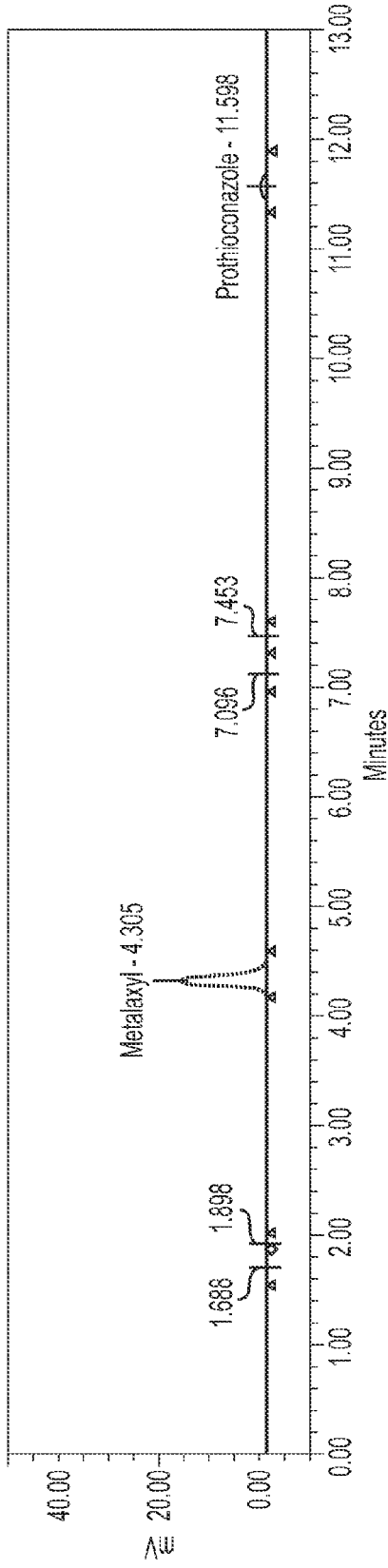
FIG. 10 describes a HPLC scan of (A) a saturated solution of metalaxyl and prothioconazole as separate compounds according to Example 5 with stirring for about 12 hours overnight at 20° C.±1° C. and (B) a cocrystallized solution of metalaxyl and prothioconazole according to Example 6 with stirring for about 12 hours overnight at 20° C.±1° C.
Figure 11A:
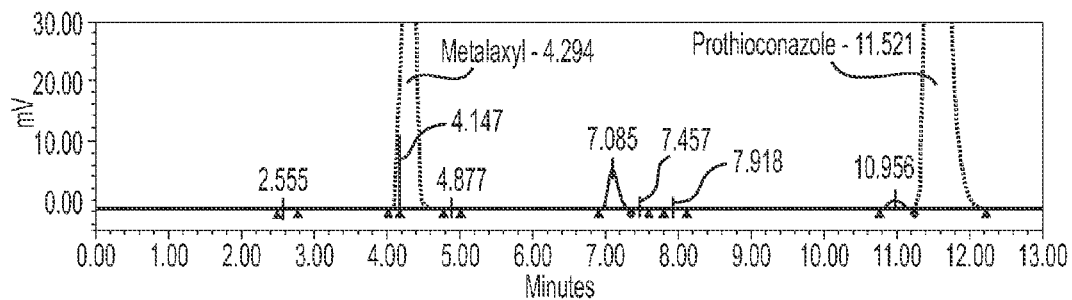
FIG. 11 describes a HPLC scan of (A) a prothioconazole and metalaxyl standard sample, (B) a saturated solution of metalaxyl and prothioconazole as separate compounds according to Example 5 with stirring for about 2 hours overnight at 20° C.±1° C., and (C) a cocrystallized solution of metalaxyl and prothioconazole according to Example 6 with stirring for about 12 hours overnight at 20° C.±1° C.
Figure 11B:
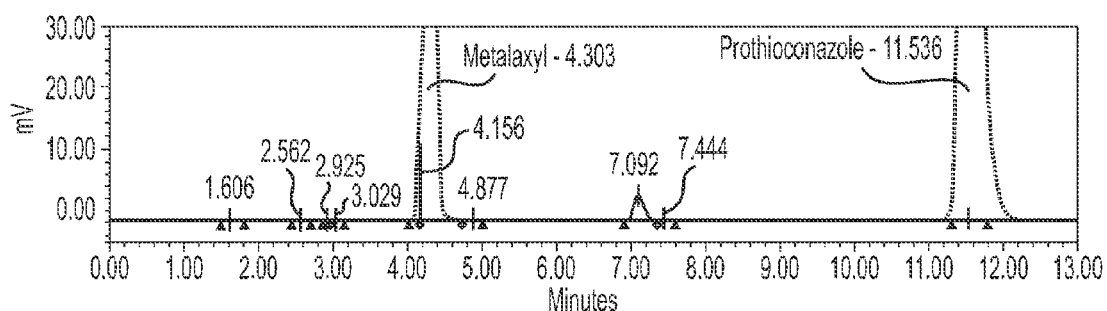

FIG. 10(A) and FIG. 11(B) provide for HPLC scans of the metalaxyl and prothioconazole compositions of Example 5.

Example 6

Example 6 provides for Metalaxyl and Prothioconazole cocrystallized water solubility measurements.

A saturated solution of metalaxyl and prothioconazole was prepared by the following procedure: 0.3 g of laboratory prepared metalaxyl-prothioconazole cocrystallized material was weighed in a 0.5 oz bottle. 10 mL of pH 7.0 (Fisher #SB107-500) was added to the bottle. A magnetic stir bar was added to the bottle and the bottle was capped and shaken. The bottle was placed on a magnetic stirrer for about 12 hours in a room at 20° C.±1° C., stirring on low. After the above procedure, the solubility of metalaxyl at pH 7.0 was measured as 0.02% and the solubility of prothioconazole at pH 7.0 was measured as 0.003%.

Figure 10B:
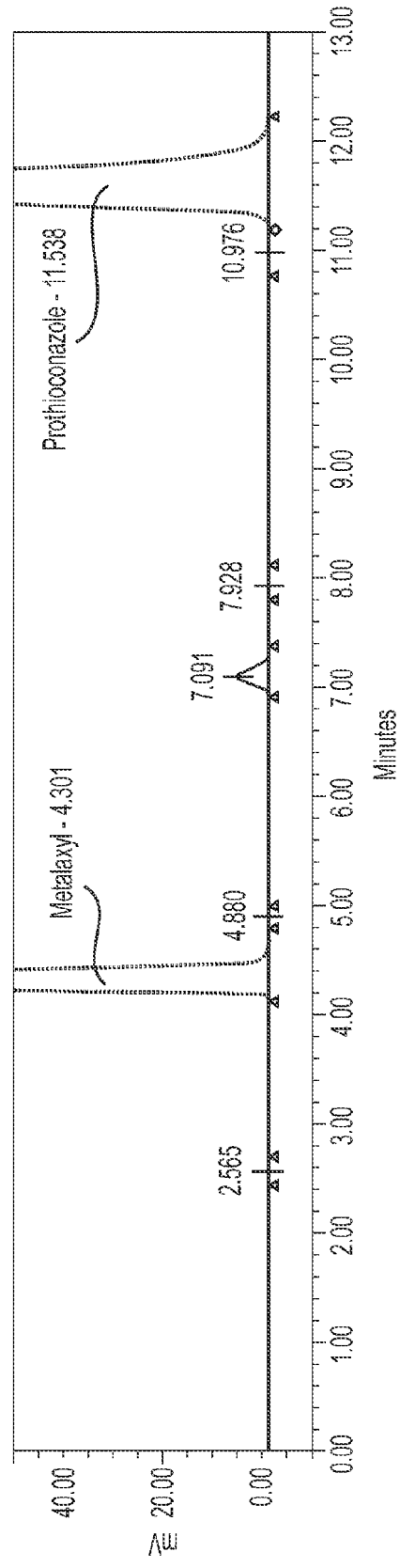
Figure 11C:
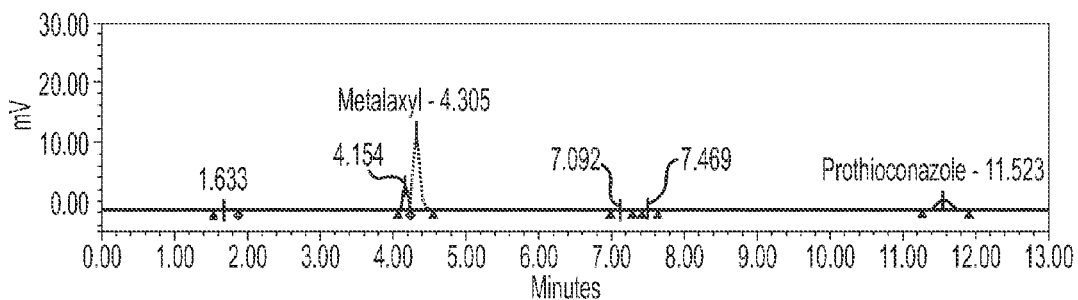

FIG. 10(B) and FIG. 11(C) provide for HPLC scans of the metalaxyl and prothioconazole cocrystalized compositions of Example 6.

Approximately 3 mL of the solutions of Example 5 and 6 were filtered through a 0.45 µM polytetrafluoroethylene ("PTFE") filter. 2.0 mL of these solutions were pipetted into separate 10 mL volumetric flasks. 3 mL of acetonitrile ("ACN") was added to each flask and diluted to volume with water. The analytical standard material of metalaxyl and prothioconazole were used as follows for the analysis of examples 5 and 6 as follows:

Metalaxyl—0.1010 g/100 mL (30 mL ACN then $H_2O$); purity of 98.2%

Prothioconazole—0.1008 g/100 mL (30 mL ACN then $H_2O$); purity of 98.4%

Example 7

Example 7 provides for Metalaxyl and Prothioconazole water solubility measurements as measured by HPLC.

The solutions of Examples 5 and 6 were diluted 2/10 into acetonitrile were injected using the following instrument conditions:

Instrument: Shimadzu LC-10A
Column: Kromasil C18 (5 μM) 250×4.6 mm
Detector: UV @ 220 nm
Mobile Phase: 55:45:0.1 ACN: $H_2O$: $H_3PO_4$
Mobile Phase Flow: 1.5 ml/min
Injections: 5 μL
Run Time: 13 minutes The cocrystallized material exhibited about a 30 fold decrease in metalaxyl solubility and about a 13 fold increase in prothioconazole solubility at pH 7.0 as compared to metalaxyl and prothioconazole compounds alone.

The invention claimed is:

1. A cocrystal consisting of prothioconazole and metalaxyl, wherein said cocrystal has a water solubility less than the water solubility of metalaxyl alone.

2. The cocrystal of claim 1, wherein said cocrystal has a melting point of about 100.8° when measured with a Differential Scanning Calorimeter.

3. The cocrystal of claim 1, wherein the diameter of said cocrystal is about 0.1 μm to about 100 μm.

4. The cocrystal of claim 1, wherein said cocrystal exhibits the Differential Scanning Calorimeter profile of FIG. 5 when crystallized from butyrolactone.

5. The cocrystal of claim 1, wherein said cocrystal exhibits the Differential Scanning Calorimeter profile of FIG. 6 when crystallized from acetone.

6. A method of making the cocrystal of claim 1 comprising
    (a) dissolving metalaxyl and prothioconazole in a solvent; and
    (b) crystallizing the dissolved metalaxyl and prothioconazole,
wherein said cocrystal has a water solubility less than the water solubility of metalaxyl alone.

7. The method of claim 6, wherein the dissolved metalaxyl and prothioconazole is crystallized in step (b) by the addition of water.

8. The method of claim 6, wherein the dissolved metalaxyl and prothioconazole is crystallized in step (b) by freezing.

9. The method of claim 6, wherein the dissolved metalaxyl and prothioconazole is crystallized in step (b) by seeding a solution with preformed metalaxyl and prothioconazole cocrystals.

10. The method of claim 6, wherein said cocrystal has a melting point at about 100.8° when measured with a Differential Scanning Calorimeter.

11. A method of reducing damage or infestation to a crop caused by weeds, fungi, or pests by applying the cocrystal of claim 1 to said crop or its environment.

12. The method of claim 11, wherein said cocrystal is applied to a crop from about 0.5 fluid ounces/acre to about 10.0 fluid ounces/acre.

13. The method of claim 11, wherein said crop is selected from the group consisting of cereals, barley, wheat, winter wheat, triticale winter rye, ground nut, peanuts, rape, bulb onions, oilseed rape, canola, rice, pulses, soybeans, sugar beet, vegetables, and corn.

14. The method of claim 11, wherein said cocrystal has a melting point of about 100.8° when measured with a Differential Scanning Calorimeter.

15. The method of claim 11, wherein the diameter of said cocrystal is about 0.1 μm to about 100 μm.

16. A composition consisting essentially of the cocrystal as claimed in claim 1.

17. The composition of claim 16, wherein said composition consists essentially of about 0.01% to about 0.5%, about 1% to about 2%, about 2% to about 4%, about 5% to about 10%, or about 20% to about 50% percent by weight of said cocrystal.

18. A method of reducing damage or infestation to a crop caused by weeds, fungi, or pests by applying the composition according to claim 16 to said crop or its environment.

19. The composition of claim 16, wherein the composition has a water solubility that is reduced by about 90% or more relative to a water solubility of metalaxyl alone.

20. The composition of claim 16, wherein said composition consists essentially of about 0.1% to about 90% percent by weight of said cocrystal.

* * * * *